United States Patent
Yoon

(10) Patent No.: US 10,028,650 B2
(45) Date of Patent: Jul. 24, 2018

(54) DEVICE FOR THREE DIMENSIONAL ENDOSCOPIC SURGERY

(75) Inventor: Cheesoon Yoon, Daejeon (KR)

(73) Assignee: CATHOLIC KWANDONG UNIVERSITY INDUSTRY FOUNDATION, Gangwon-do (KR)

(*) Notice: Subject to any disclaimer, the term of this patent is extended or adjusted under 35 U.S.C. 154(b) by 651 days.

(21) Appl. No.: 14/398,456

(22) PCT Filed: Aug. 30, 2012

(86) PCT No.: PCT/KR2012/006913
§ 371 (c)(1),
(2), (4) Date: Nov. 1, 2014

(87) PCT Pub. No.: WO2013/100312
PCT Pub. Date: Jul. 4, 2013

(65) Prior Publication Data
US 2015/0265143 A1    Sep. 24, 2015

(30) Foreign Application Priority Data

Dec. 26, 2011   (KR) .................. 10-2011-0142323

(51) Int. Cl.
*A61B 1/04*    (2006.01)
*A61B 1/00*    (2006.01)
(Continued)

(52) U.S. Cl.
CPC ........ *A61B 1/3132* (2013.01); *A61B 1/00087* (2013.01); *A61B 1/00128* (2013.01);
(Continued)

(58) Field of Classification Search
CPC .............. A61B 1/0008; A61B 1/00087; A61B 1/00096; A61B 1/00163; A61B 1/00174;
(Continued)

(56) References Cited

U.S. PATENT DOCUMENTS 5,166,787 A * 11/1992 Irion .................. A61B 1/00181
                                                348/75
5,782,752 A *  7/1998 Lichtman ............. A61B 1/0052
                                                600/129
(Continued)

FOREIGN PATENT DOCUMENTS

JP    2005027851 A    2/2005
JP    10-2011-0104234 A    9/2011
KR    10-2008-0027187 A    3/2008

OTHER PUBLICATIONS

International Search Report for PCT/KR2012/006913.

*Primary Examiner* — John P Leubecker
*Assistant Examiner* — Pamela F Wu
(74) *Attorney, Agent, or Firm* — Harness, Dickey & Pierce, P.L.C.

(57) ABSTRACT

The present invention relates to a device for three dimensional endoscopic surgery, and more specifically, to a device for three dimensional endoscopic surgery, wherein therapeutic tools including an endoscope can be inserted into the human body through one main tube, and the therapeutic tools can be spread outward to be utilized in the human body, thereby minimizing an incision site in case of surgical operation while allowing various medical operations to be performed using one main tube. The present invention is a device for endoscopic surgery comprising: a main tube which is inserted into the body of a patient; first and second cameras which are inserted in a row into the main tube; a light source portion which is inserted between the first and second cameras; and a therapeutic tool which is located below the second camera to be inserted into the main tube.

17 Claims, 15 Drawing Sheets

(51) Int. Cl.
*A61B 1/313* (2006.01)
*A61B 1/05* (2006.01)
*A61B 1/06* (2006.01)
*A61B 1/12* (2006.01)
*A61B 17/00* (2006.01)
*A61B 90/30* (2016.01)
*A61B 90/00* (2016.01)
*A61B 34/30* (2016.01)

(52) U.S. Cl.
CPC ...... *A61B 1/00181* (2013.01); *A61B 1/00193* (2013.01); *A61B 1/051* (2013.01); *A61B 1/0676* (2013.01); *A61B 1/126* (2013.01); *A61B 17/00234* (2013.01); *A61B 90/30* (2016.02); *A61B 90/361* (2016.02); *A61B 90/37* (2016.02); *A61B 34/30* (2016.02); *A61B 2017/0034* (2013.01); *A61B 2017/00296* (2013.01); *A61B 2034/302* (2016.02); *A61B 2090/309* (2016.02); *A61B 2090/371* (2016.02)

(58) Field of Classification Search
CPC ............ A61B 1/00177; A61B 1/00179; A61B 1/00181; A61B 1/00183; A61B 1/0125; A61B 1/00193; A61B 1/04; A61B 1/041; A61B 1/05; A61B 1/051; A61B 1/053; A61B 1/3132
USPC ........ 600/111, 104, 106, 109, 110, 112, 127, 600/129, 160–181
See application file for complete search history.

(56) References Cited

U.S. PATENT DOCUMENTS

| | | | |
|---|---|---|---|
| 8,403,826 B1 * | 3/2013 | Zobel | A61B 1/05 600/109 |
| 2003/0164952 A1 | 9/2003 | Deichmann | |
| 2005/0234294 A1 * | 10/2005 | Saadat | A61B 1/0008 600/104 |
| 2006/0025650 A1 * | 2/2006 | Gavriely | A61B 1/00057 600/110 |
| 2008/0071288 A1 | 3/2008 | Larkin | |
| 2009/0112207 A1 * | 4/2009 | Walker | A61B 17/7016 606/57 |
| 2011/0238054 A1 * | 9/2011 | Kim | A61B 18/1815 606/33 |

* cited by examiner

DEVICE FOR THREE DIMENSIONAL ENDOSCOPIC SURGERY

TECHNICAL FIELD

The present invention relates to a device for three-dimensional endoscopic surgery, and more specifically, to a device for three-dimensional endoscopic surgery in which surgical instruments including an endoscope can be inserted into the human body through one main tube and can be spread outward to be utilized in the human body, thereby minimizing an incision site at the time of surgery and performing various medical works using one main tube.

BACKGROUND ART

In general, an endoscope refers to a medical instrument which is used to directly look inside internal organs or body cavities, and is an instrument which has been made to be inserted into an organ of which a lesion cannot be directly observed without surgery or autopsy and enables observation of the lesion.

In order to solve problems of the conventional laparotomy in which an abdominal site is incised with a knife, the endoscopy operation has been recently developed and conducted such that small holes are perforated without the incision of the abdominal site and special instruments are inserted into the holes, followed by surgery. However the conventional laparotomy has a disadvantage in that a total of four incision windows are needed since an endoscope for photographing a lesion site, an instrument for performing surgery, and assisting devices need to be respectively inserted, as shown in FIG. 1.

In order to solve the problem, devices capable of simultaneously accommodating an endoscope and surgical instruments in one tube have been used. These devices have an advantage in that works such as treatment and surgery can be performed using only one incision window since tubes into which a carrier for transmitting images, that is, an optical fiber or a camera, an optical fiber for illuminating, and instruments for performing works such as treatment and surgery under the induction of the endoscope are installed in one tube. However, since the instruments are linearly installed on one plane, the diameter of the tube needs to be enlarged.

In other words, although the recent medical demand is that the cross-sectional area of the endoscope is made as small as possible so that diagnosis or treatment is performed using a natural opening (nasal cavity or throat) or a small incision window in a non-invasive or less invasive manner, the foregoing method has a disadvantage in that the area to be incised is increased at the time of surgery.

In order to solve the problem, Korean Patent Application Publication No. 10-2011-0104234 discloses an electronic endoscope providing three-dimensional image data. The main technical configuration thereof is that, as shown in FIG. 2, the endoscope has a pipe-shaped body (13) which is inserted into the patient's body to provide image information, wherein the pipe-shaped body (13) includes: a tip part (11) having an opened tip; a bendable part (12) connected to the tip part (11), and being bent when the tip part (11) is inserted into the patient's body; a first photographing part (14) installed at one side surface inside the tip part (11), being operable in an up-and-down direction and in a rotational direction by interlocking with the operation of a first operating rod (17) connected to a lower end thereof, and having a photographing device (16) installed at a front surface thereof; and a second photographing part (15) installed at the other side surface inside the tip part (11), being operable in an up-and-down direction and in a rotational direction by interlocking with the operation of a second operating rod (18) connected to a lower end thereof, and having a photographing device (16) installed at a front surface thereof.

The foregoing configuration has an advantage in that two photographing parts and an illuminating parts for photographing three-dimensional images are folded inside the pipe-shaped body and the photographing parts are spread in the human body, so that the diameter of the body is decreased, thereby minimizing the incision at the surgical site, but has a disadvantage in that an incision window through which instruments necessary for treatment and surgery can be inserted needs to be further formed.

The foregoing configuration also has a disadvantage in that, since a separate device for washing the photographing parts is not prepared, a photographed image cannot be differentiated in cases where foreign substances are attached on lenses of the photographing parts inserted into the body.

SUMMARY

Therefore, the present invention has been made in view of the above-mentioned problems, and an aspect of the present invention is to provide a device for three-dimensional endoscopic surgery in which therapeutic instruments including an endoscope can be inserted into the human body through one main tube and can be spread outward to be utilized in the human body, thereby enabling surgery through a natural opening such as a nasal cavity or throat, minimizing an incision site at the time of surgery, and performing various medical works using one main tube.

Another aspect of the present invention is to provide a device for three-dimensional endoscopic surgery in which various functional instruments are inserted into the human body using one main tube, thereby requiring no additional incision window.

Still another aspect of the present invention is to provide a device for three-dimensional endoscopic surgery in which an endoscope consisting of a camera and a light source and therapeutic instruments for performing medical works are sequentially inserted inside a main tube, so that larger therapeutic instruments can be installed inside the main tube, thereby performing various medical works.

Still another aspect of the present invention is to provide a device for three-dimensional endoscopic surgery in which a large camera is installed inside a main tube, and washing modules for washing cameras and a light source are provided inside the main tube, thereby providing clearer three-dimensional images during performing of medical works.

In accordance with an aspect of the present invention, there is provided a device for three-dimensional endoscopic surgery, including: a main tube inserted into the patient's body; first and second cameras inserted in a line inside the main tube; a light source part inserted between the first and second cameras; and a therapeutic instrument positioned below the second camera and inserted inside the main tube.

Here, first and second assisting devices may be inserted between the second camera and the therapeutic instrument.

The main tube may consist of an inner tube and an outer tube, and first to fifth shafts respectively coupled with the first and second cameras, the light source part, and the first and second assisting devices may be inserted between the inner tube and the outer tube.

The first to fifth shafts may be respectively connected to the first and second cameras, the light source part, and the first and second assisting devices by connection members, installation holes with which the first to fifth shafts may be insert-coupled are formed in an inner circumferential surface of the outer tube, and guide slits with which the connection members may be insert-coupled are formed in the inner tube.

Here, fixing grooves with which the connection members are fit-coupled may be formed in an outer circumferential surface of an upper end of the outer tube.

Here, coupling holes with which the shafts are insert-coupled may be formed in the first and second cameras, the light source part, and the first and second assisting devices.

Each of the first to fifth shafts may include a first tube connected to each of the first and second cameras, the light source part, and the first and second assisting devices and a second tube inserted inside the first tube.

Here, a signal transmission conductor for transmitting image signals and driving signals may be inserted between the first tube and the second tube.

The first and second tubes may be formed of an insulation-coated titanium pipe.

The first and second cameras may include lens mounts on which lenses are fixed, image sensors installed at the rear of the lenses, and lens driving devices positioned at the rear of the image sensors and connected to the lens mounts.

The image sensors may consist of photosensors at the center thereof and signal connectors provided outside the photosensors, the signal connectors being bent in opposite directions of the lenses.

Here, washing modules for washing lenses and may be provided in the first and second cameras and the light source parts.

Here, permanent magnets may be insert-coupled with outer circumferential surfaces of the first to fifth shafts and electronic magnets having coils wound thereon are provided inside the outer tube spaced apart from the permanent magnets at predetermined intervals.

Here, locking devices may be connected to the first to fifth shafts for preventing rotation of the first to fifth shafts.

Each of the locking devices may include a connector inserted into each of the first to fifth shafts, a locking lever connected to the connector, and a locking tube having a '¬'-shaped lever groove in which the locking lever is moved.

The first and second assisting devices may be formed of robotic arms.

According to the present invention, therapeutic instruments including an endoscope can be inserted into the human body through one main tube and can be spread outward to be utilized in the human body, thereby minimizing an incision site at the time of surgery, utilizing natural openings without separate incision windows, and performing various medical works using one main tube.

Further, according to the present invention, an endoscope consisting of a camera and a light source and therapeutic instruments for performing medical works are sequentially inserted inside a main tube, so that larger therapeutic instruments can be installed inside the main tube, thereby performing various medical works.

Further, according to the present invention, large-diameter cameras can be installed inside a main tube, and washing modules for washing cameras and a light source can be provided inside the main tube, thereby providing clearer three-dimensional images during performing of medical works

DETAILED DESCRIPTION

Hereinafter, preferable embodiments of a device for three-dimensional endoscopic surgery according to the present invention will be described in detail with reference to the accompanying drawings.

Figure 3:
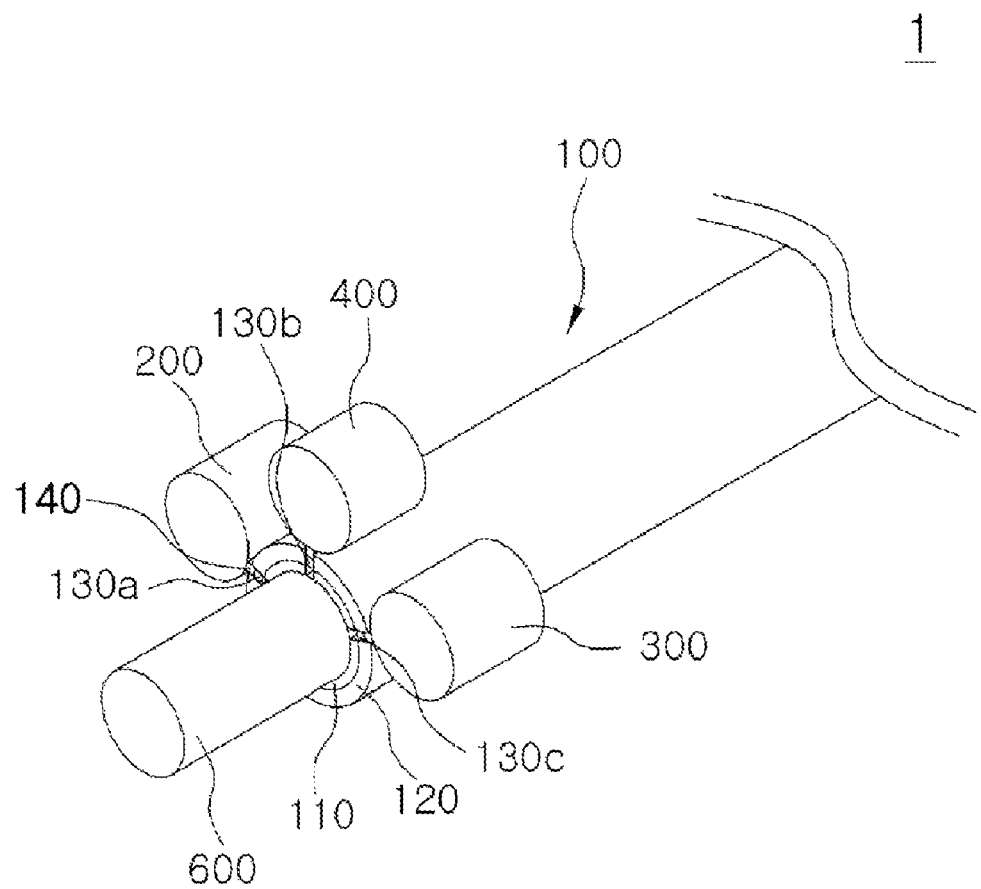
FIG. 3 is a perspective view showing a device for three-dimensional endoscopic surgery according to an embodiment of the present invention.
Figure 4:
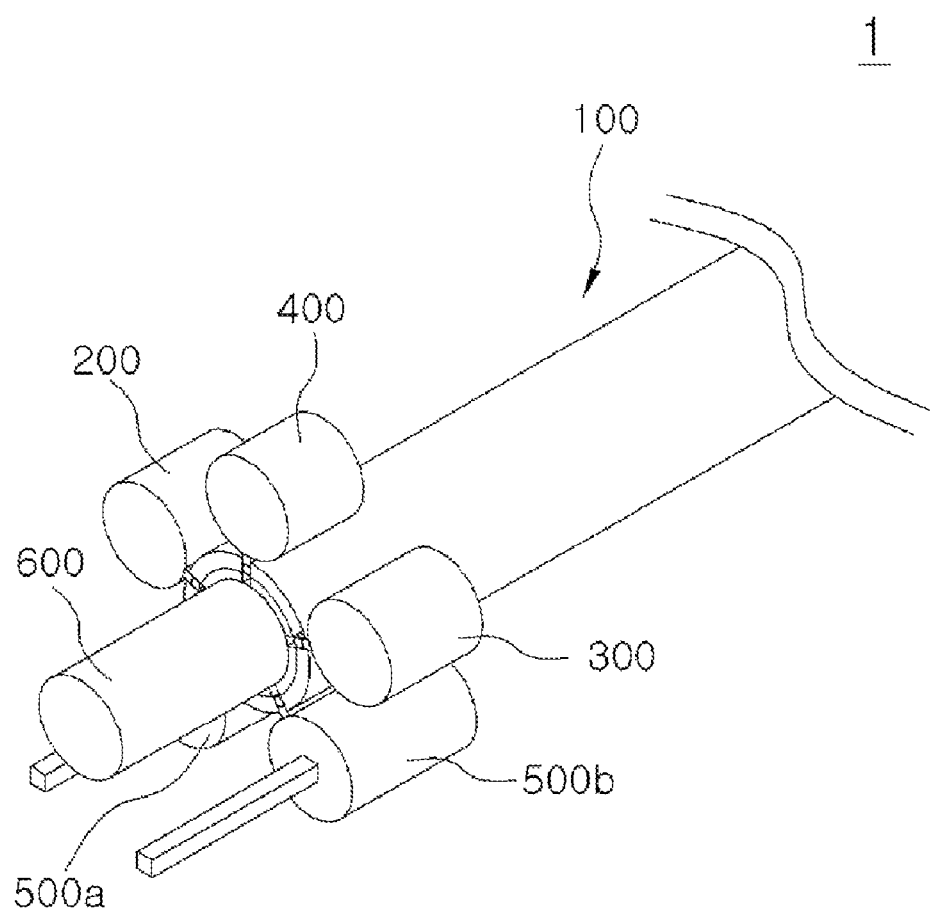
FIG. 4 is a perspective view showing a device for three-dimensional endoscopic surgery according to another embodiment of the present invention.
Figure 5:
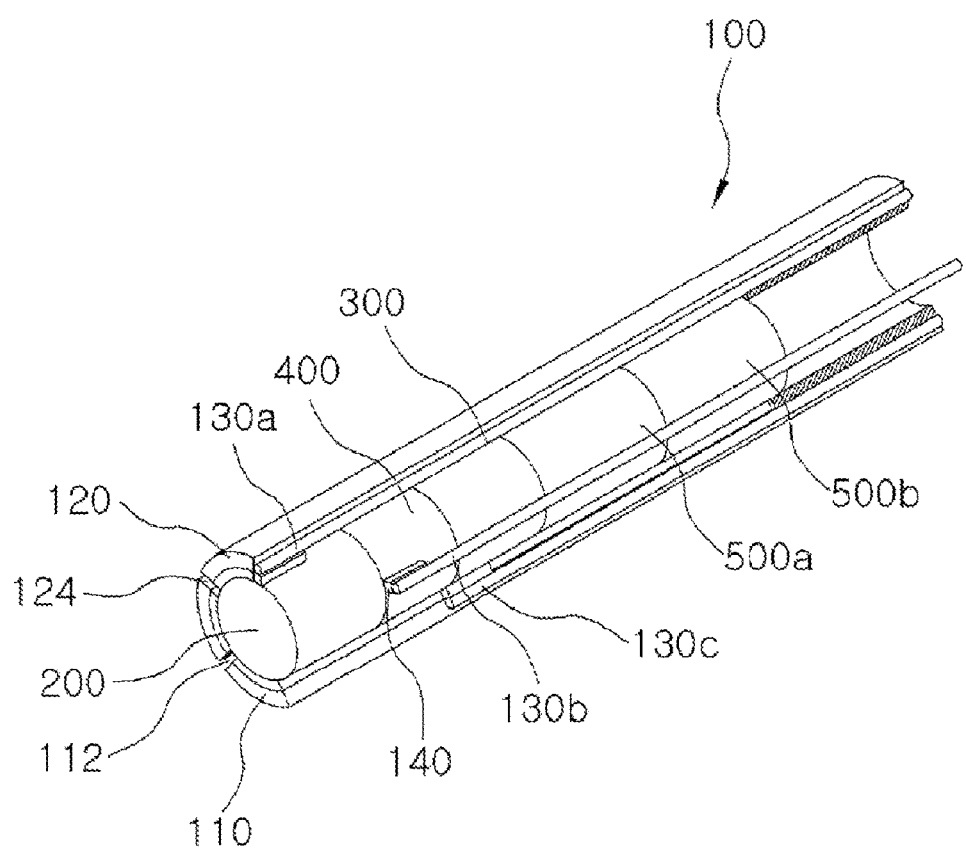
FIG. 5 is a partial cross-sectional view showing a main tube and an inner structure thereof.
Figure 6A:
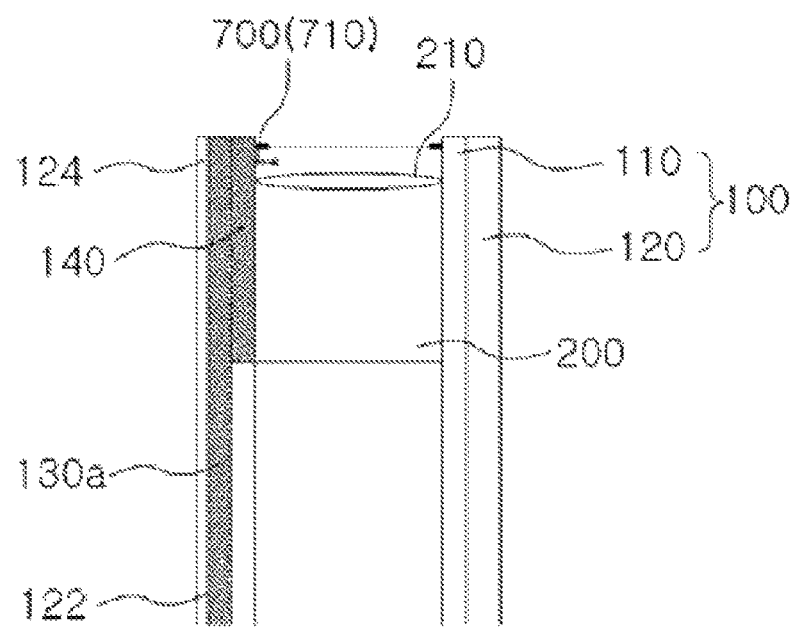
FIGS. 6(a) and (b) are partial cross-sectional views schematically showing a structure of a main tube in a device for three-dimensional endoscopic surgery according to the present invention.
Figure 7:
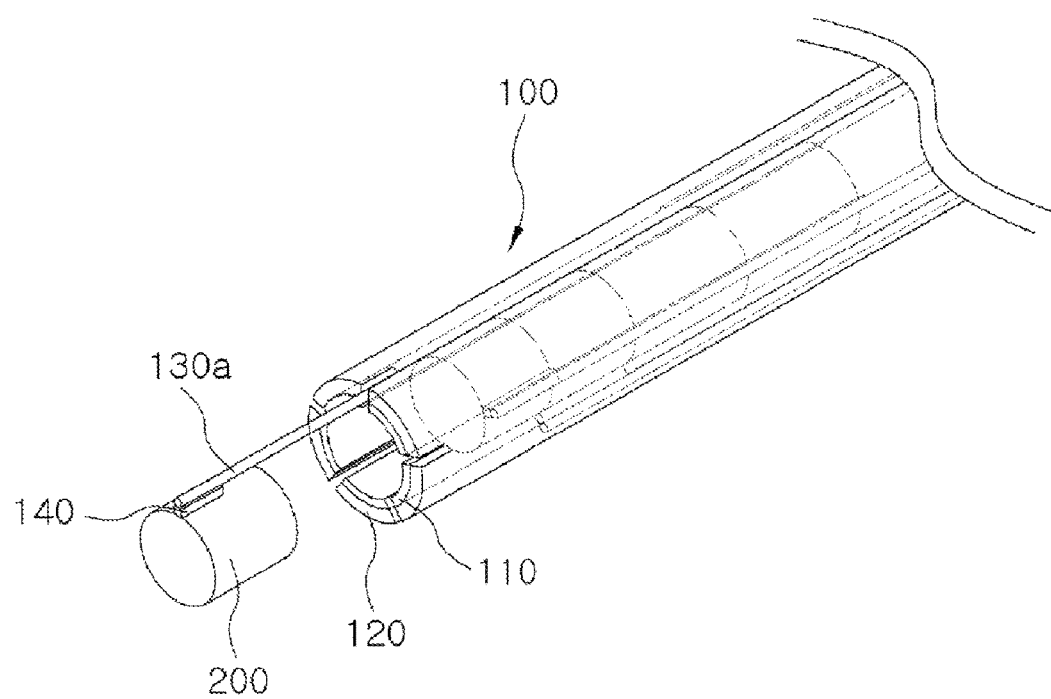
FIGS. 7 and 8 are perspective views illustrating an operative relationship of a device for three-dimensional endoscopic surgery according to the present invention.
Figure 8:
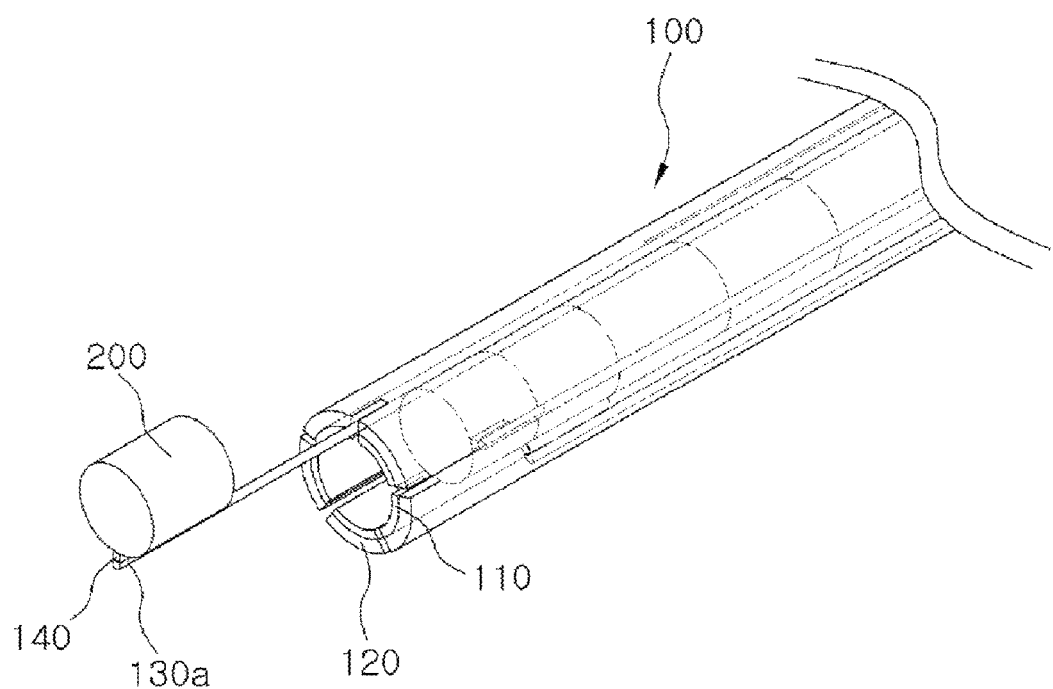
Figure 9:
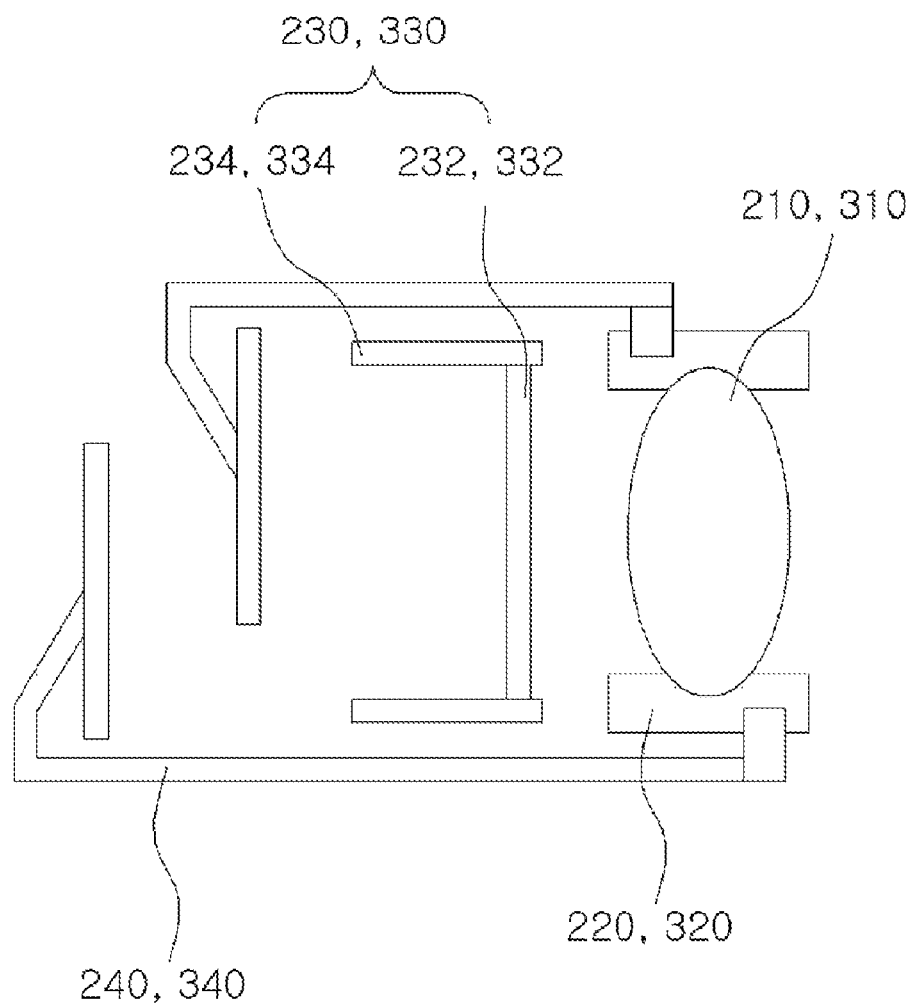
FIG. 9 is a cross-sectional view schematically showing inner structures of a first camera and a second camera in a device for three-dimensional endoscopic surgery according to the present invention.
Figure 10A:
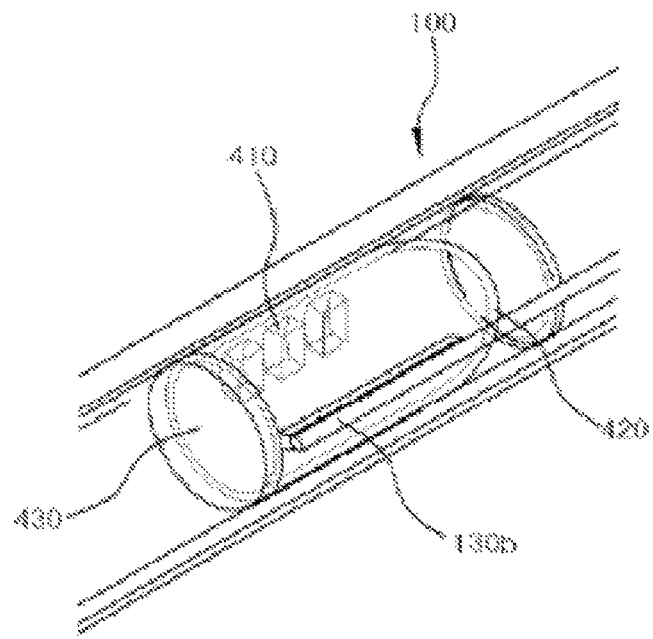
FIGS. 10(a) and (b) are a perspective view and a cross-sectional view schematically showing an inner structure of a light source part in a device for three-dimensional endoscopic surgery according to the present invention.
Figure 11:
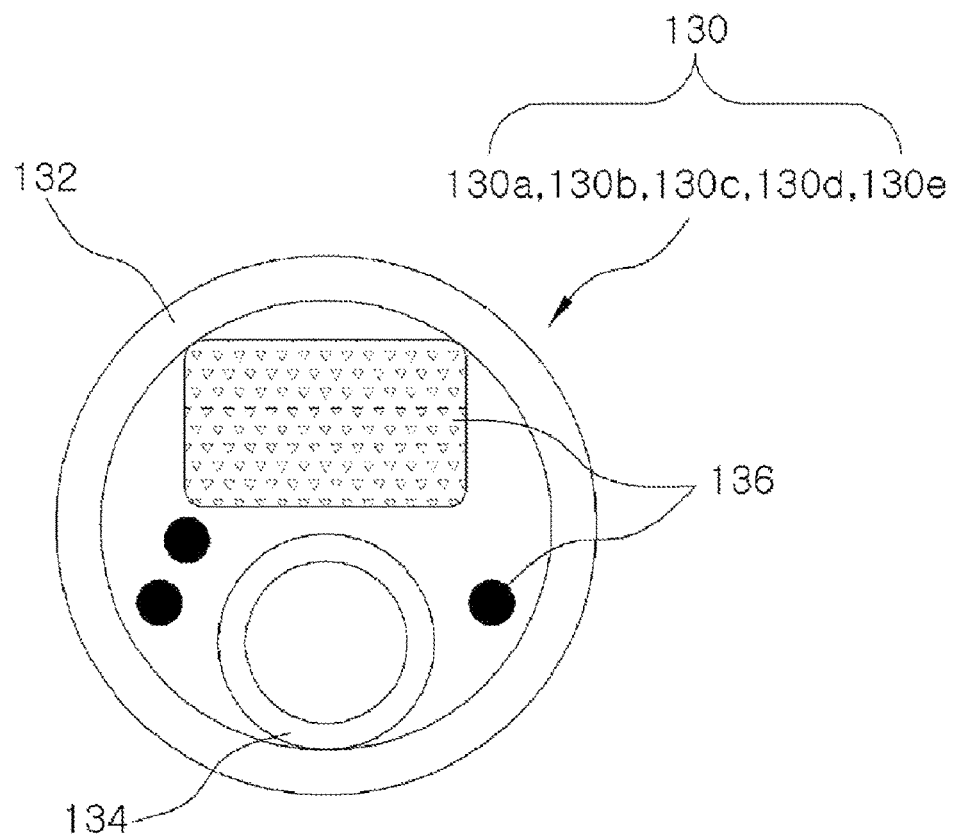
FIG. 11 is a cross-sectional view concretely showing a structure of a shaft in a device for three-dimensional endoscopic surgery according to the present invention.
Figure 12A:
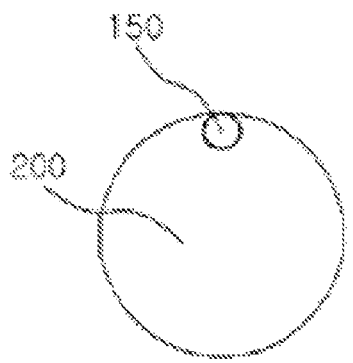
FIG. 12(a) to (e) are plane views conceptually showing another example of each of first and second cameras, a light source part, and first and second assisting devices in a device for three-dimensional endoscopic surgery according to the present invention.
Figure 12B:
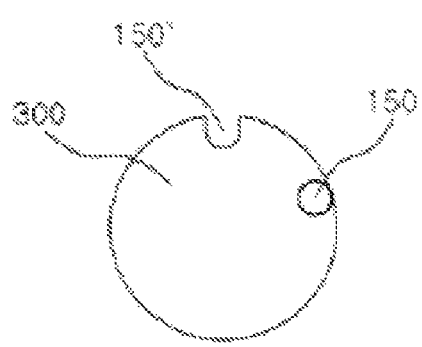
Figure 12C:
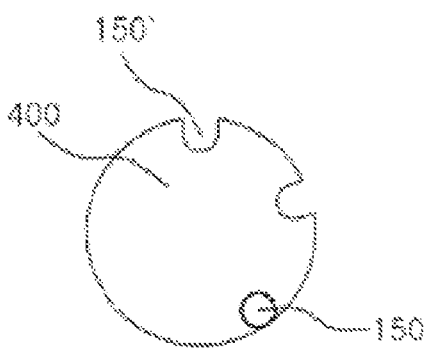
Figure 12D:
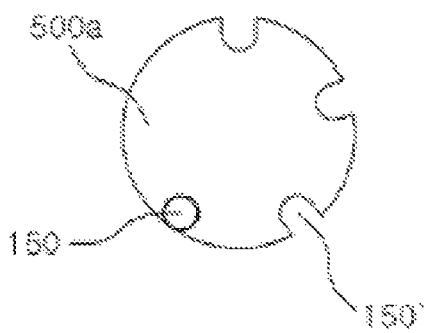
Figure 12E:
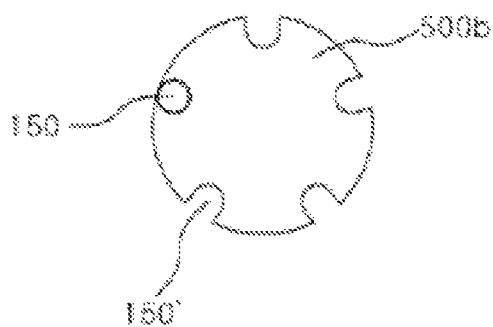
Figure 13:
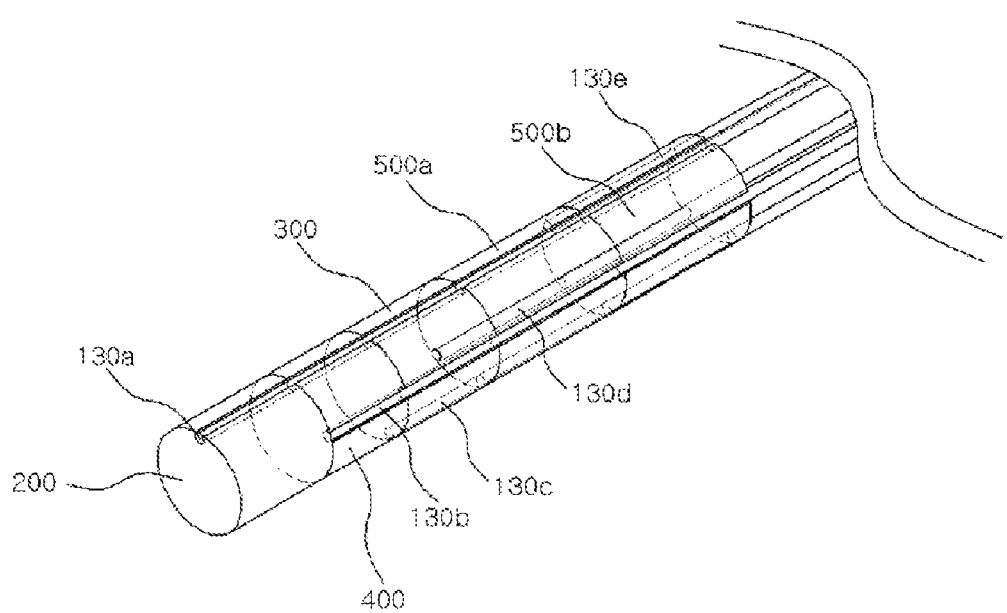
FIG. 13 is a perspective view conceptually showing another example of each of the first and second cameras, the light source part, and the first and second assisting devices in the device for three-dimensional endoscopic surgery according to the present invention.
Figure 14A:
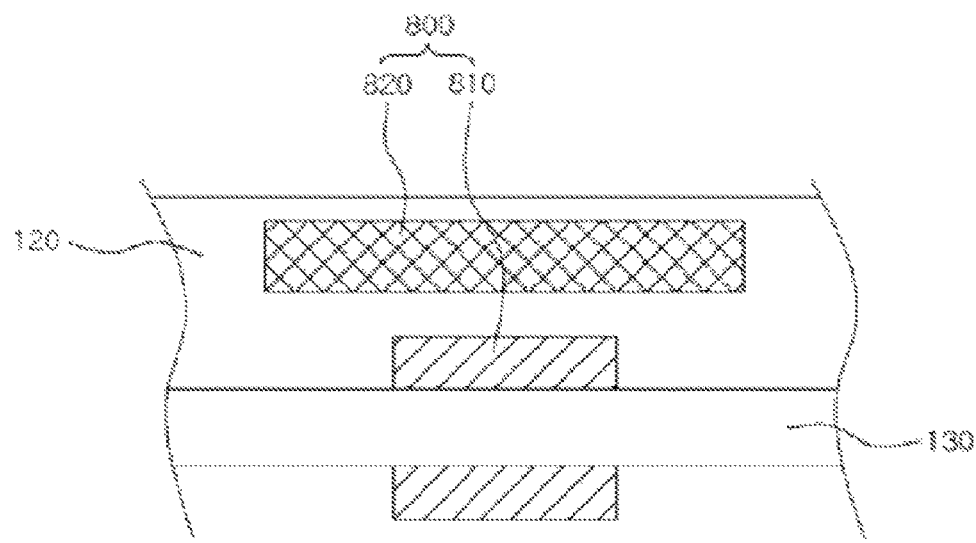
FIGS. 14(a) and (b) are a cross-sectional view and a partial perspective view schematically showing a rotation driving device in a device for three-dimensional endoscopic surgery according to the present invention.
Figure 14B:
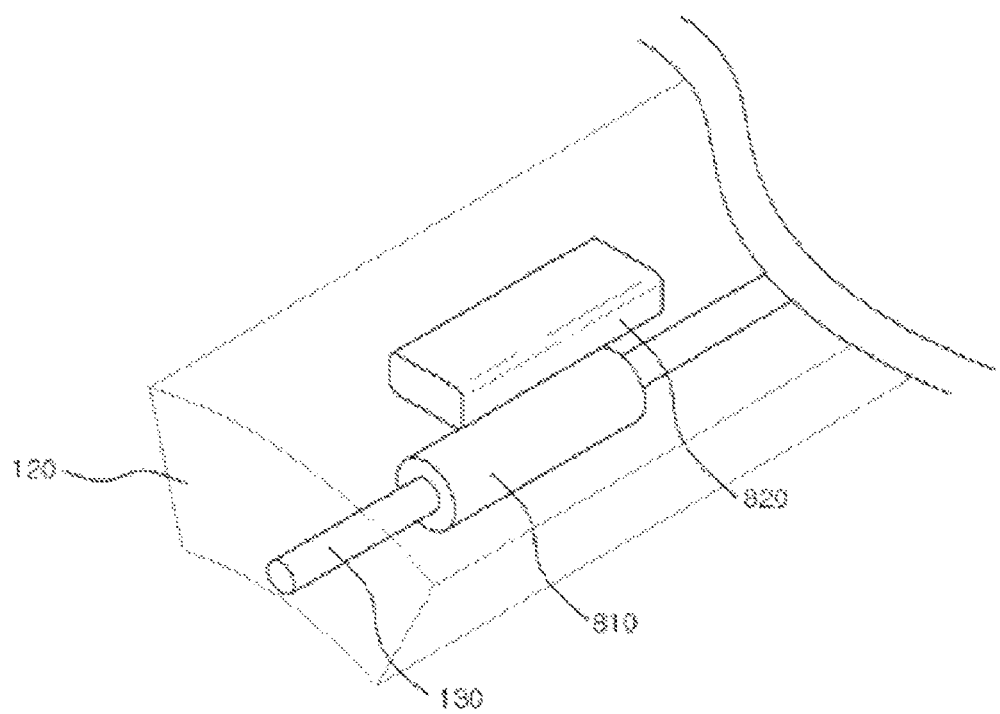
Figure 15A:
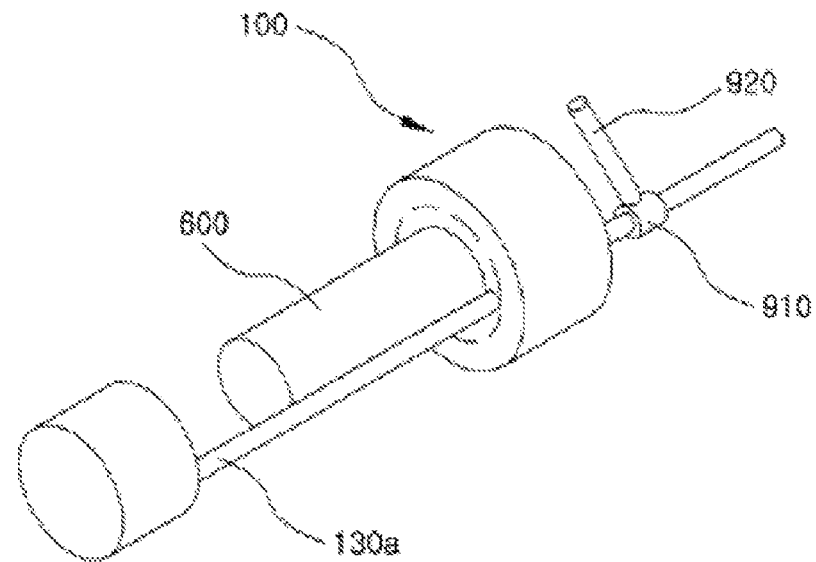
FIGS. 15(a) and (b) are partial cross-sectional views schematically showing a locking device in a device for three-dimensional endoscopic surgery according to the present invention.
Figure 15B:
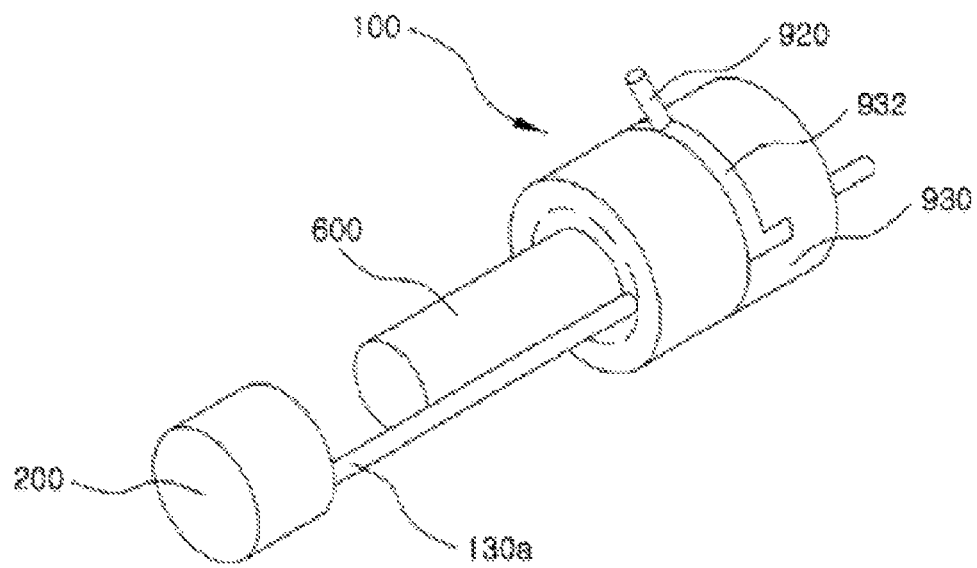

FIG. 3 is a perspective view showing a device for three-dimensional endoscopic surgery according to an embodiment of the present invention; FIG. 4 is a perspective view showing a device for three-dimensional endoscopic surgery according to another embodiment of the present invention; FIG. 5 is a partial cross-sectional view showing a main tube and an inner structure thereof; FIGS. 6(a) and (b) are partial cross-sectional views schematically showing a structure of a main tube in a device for three-dimensional endoscopic surgery according to the present invention; FIGS. 7 and 8 are perspective views illustrating an operative relationship of a device for three-dimensional endoscopic surgery according to the present invention; FIG. 9 is a cross-sectional view schematically showing inner structures of a first camera and a second camera in a device for three-dimensional endoscopic surgery according to the present invention; FIGS. 10(a) and (b) are a perspective view and a cross-sectional view schematically showing an inner structure of a light source part in a device for three-dimensional endoscopic surgery according to the present invention; FIG. 11 is a cross-sectional view concretely showing a structure of a shaft in a device for three-dimensional endoscopic surgery according to the present invention; FIG. 12(a) to (e) are plane views conceptually showing another example of each of first and second cameras, a light source part, and first and second assisting devices in a device for three-dimensional endoscopic surgery according to the present invention; FIG. 13 is a perspective view conceptually showing another example of each of the first and second cameras, the light source part, and the first and second assisting devices in the device for three-dimensional endoscopic surgery according to the present invention; FIGS. 14(a) and (b) are a cross-sectional view and a partial perspective view schematically showing a rotation driving device in a device for three-dimensional endoscopic surgery according to the present invention; FIGS. 15(a) and (b) are partial cross-sectional views schematically showing a locking device in a device for three-dimensional endoscopic surgery according to the present invention.

The present invention is directed to a device for three-dimensional endoscopic surgery 1 in which surgical instruments including an endoscope can be inserted into the human body through one main tube 100 and can be spread outward to be utilized in the human body, thereby minimizing an incision site at the time of surgery and performing various medical works using one main tube 100. The device for three-dimensional endoscopic surgery 1 largely includes a main tube 100, first and second cameras 200 and 300, a light source part 400, and a therapeutic instrument 600, as shown in FIG. 3.

More specifically, the main tube 100 has a space part formed inside thereof, and the cameras 200 and 300, the light source part 400, and the therapeutic instrument 600 may be accommodated in a line in the space part, so that the main tube 100 can serve to insert the instruments into the human body. The main tube 100 is formed of a smooth flexible material.

Figure 6B:
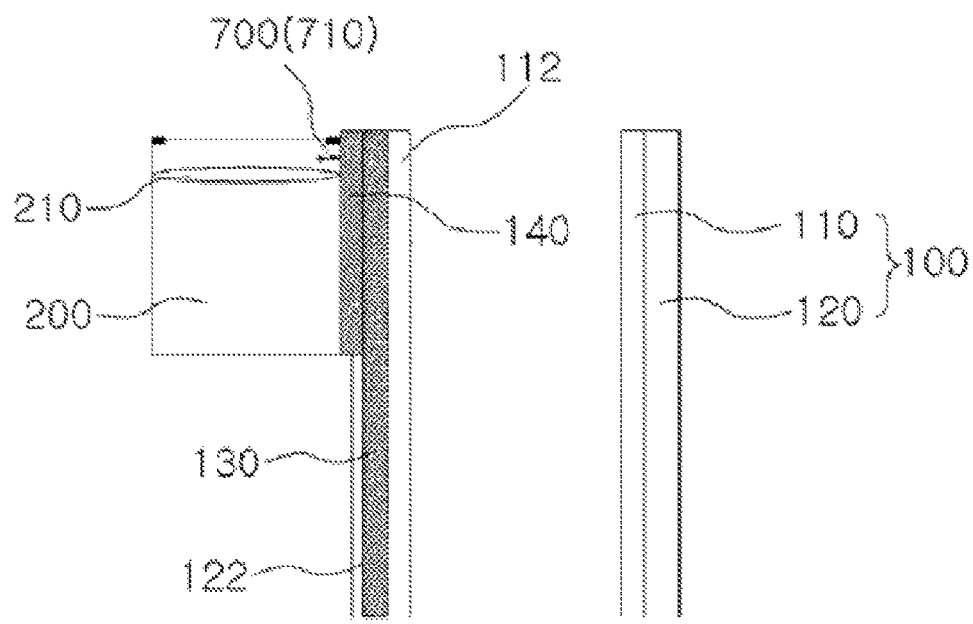

Here, as shown in FIGS. 5 and 6, the main tube 100 is formed in a double structure including an inner tube 110 and an outer tube 120. The inner tube 110 serves to provide a space in which the first and second cameras 200 and 300, the light source part 400, and the therapeutic instrument 600 can be inserted in a line and to guide and support the forward and backward movement of the first and second cameras 200 and 300, the light source part 400, and the therapeutic instrument 600. The outer tube 120 is closely attached on an outside of the inner tube 110, and serves to support the inner tube 110 and to provide a space part in which shafts 130 to be later described are inserted to be able to rotate.

On the other hand, the first and second cameras 200 and 300 are inserted in a line inside the main tube 100. While the main tube 100 is inserted in the human body, the first and second cameras 200 and 300 serve to photograph an internal portion of the patient's body in three-dimensional images by protruding outwardly from the main tube 100 by the operation of the shafts 130 to be later described.

That is, since two focuses are needed in order to obtain a three-dimensional image by the endoscope, the two cameras 200 and 300 are configured to photograph the internal portion of the patient's body from different positions.

Here, as shown in FIG. 9, the first and second cameras 200 and 300 include lenses 210 and 310, lens mounts 220 and 230, image sensors 230 and 330, and lens driving devices 240 and 340, respectively. First, the lens mounts 220 and 320 serve to support outer circumferential surfaces of the lenses 210 and 310 to fix the lenses 210 and 310, and are slidably fixed inside a circular-shaped case (not shown) having a size corresponding to the inner diameter of the inner tube 110.

The image sensors 230 and 330 serve to convert image signals photographed from the lenses 210 and 310 into electric digital image signals, and installed to be spaced apart from the rear of the lenses 210 and 310 at predetermined intervals.

Here, the image sensors 230 and 330 include: photosensors 232 and 332 which are positioned at the center portions and sense lights at the center portions to convert the sensed lights into electric signals; and signal connectors 234 and 334 which are formed at the rest portions of the image sensors 230 and 330, that is, at outsides of the photosensors 232 and 332 and transmit the signals converted by the photosensors 232 and 332, respectively. The signal connectors 234 and 334 are bent backwardly, that is, in the opposite directions of the lenses 210 and 310.

More specifically, since the first and second cameras 200 and 300 are inserted inside the inner tube 110, the cross-sectional areas of the first and second cameras 200 and 300 inserted inside the inner tube 110 need to be minimized in order to decrease the diameter of the main tube 100 inserted into the patient's body. However, when the signal connectors 234 and 334 provided outside the photosensors 232 and 332 are positioned on the same plane as the photosensors 232 and 332, the cross-sectional areas of the first and second cameras 200 and 300 are increased. Therefore, the signal connectors 234 and 334 are bent in the opposite directions of the lenses 210 and 310 to configure the image sensors 230 and 330 in three dimensions, thereby minimizing the cross-sectional areas of the first and second cameras 200 and 300.

The lens driving devices 240 and 340 serve to drive the lenses 210 and 310 so as to allow the first and second cameras 200 and 300 to have a focus function and a zoom function, and are connected to the lens mounts 220 and 320 supporting the lenses 210 and 310.

Here, the lens driving devices 240 and 340 drive the lenses 210 and 310 by using a piezo motor, and, in order to minimize the cross-sectional areas of the first and second cameras 200 and 300, the lens driving devices 240 and 340 are positioned at the rears of the image sensors 230 and 330 and connected to the lens mounts 220 and 320.

Meanwhile, the first and second cameras 200 and 300 receive power through first and third shafts 130a and 130c to be later described, and descriptions thereof will be set forth later.

The light source part 400 is positioned between the first and second cameras 200 and 300 and inserted inside the inner tube 110 of the main tube 100, and serves to provide illumination for allowing first and second cameras 200 and 300 to photograph the internal portion of the patient's body.

Figure 10B:
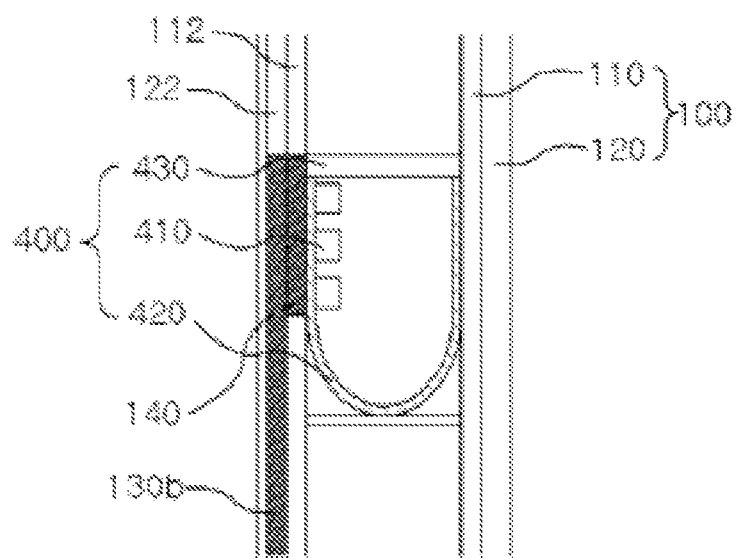

As shown in FIGS. 10a and 10b, the light source part 400 includes a plurality of LEDs 410, a reflective mirror 420, and a protective lens 430. First, the LEDs 410 serve to generate lights by receiving power through a second shaft 130 b to be later described, and are installed in parallel with each other inside a case (not shown) so as to provide a maximum illuminating effect in consideration of spatial limitations due to the installation space of the light source part.

The reflective mirror 420 serves to perform forward reflection of the lights generated from the LEDs 410, and may be installed on an inside surface and a bottom surface of the case (not shown). In order to maximize the front illuminating effect, a portion of the reflective 420, which is installed at the bottom surface, is concave so as to have a smoothly curved surface.

In addition, the protective lens 430 serves to prevent the invasion of foreign substances into the light source part 400 and perform forward projection of the lights generated from the LEDs 410, and are fixed onto an inner circumferential surface of the front end of the case (not shown).

Meanwhile, washing modules 700 may be installed at the first and second cameras 200 and 300 and the light source part 400, respectively. The washing modules 700 serve to remove foreign substances such as blood and body fluid, which are smeared on surfaces of the lenses 210 and 310 or the protective lens 430 during the therapeutic procedure.

That is, passages through which fluid such as air or water can pass are formed inside the shafts 130 to be later described, and the fluid supplied through the shafts 130 is sprayed on the lenses 210 and 310 provided in the first and second cameras 200 and 300 or the protective lens 430 provided in the light source part 400 to clean the surfaces of the lenses 210 and 310 or the protective lens 430, thereby preventing the images photographed by the first and second cameras 200 and 300 from being hard to see or preventing the lights generated from the light source part 400 from failing to be transmitted to the outside, due to the foreign substances.

These washing modules 700 may be configured such that spray nozzles 710 are connected to the shafts 130 respectively installed at the first and second cameras 200 and 300 and the light source part 400. Here, head portions of the spray nozzles 710 for spraying fluid such as air or water are bent toward the lenses 210 and 310 or the protective lens 430.

The therapeutic instrument 600 serves to perform various surgical operations by being inserted in the patient's body, and is inserted into the innermost portion inside the inner tube 110 of the main tube 100.

Figure 1:
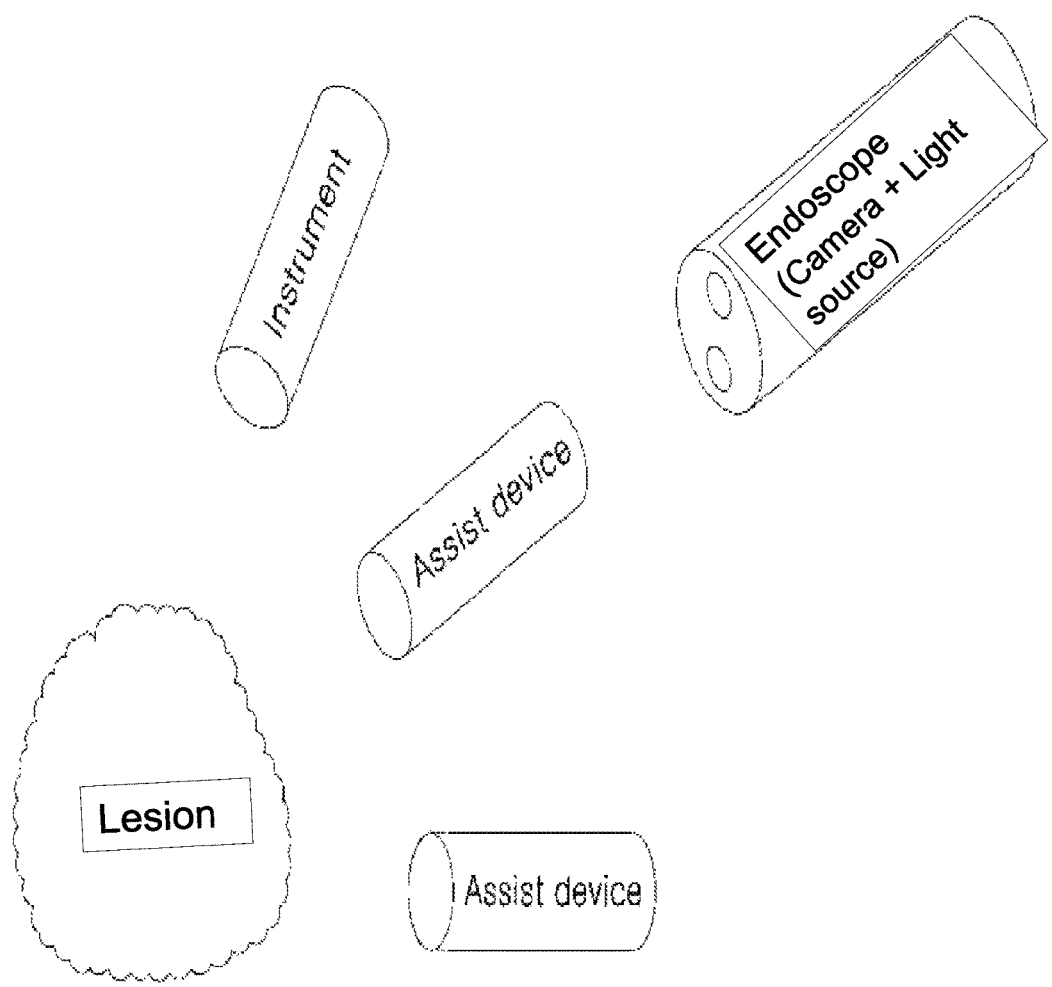
FIG. 1 is a diagram conceptually showing a conventional endoscopic surgery system.
Figure 2:
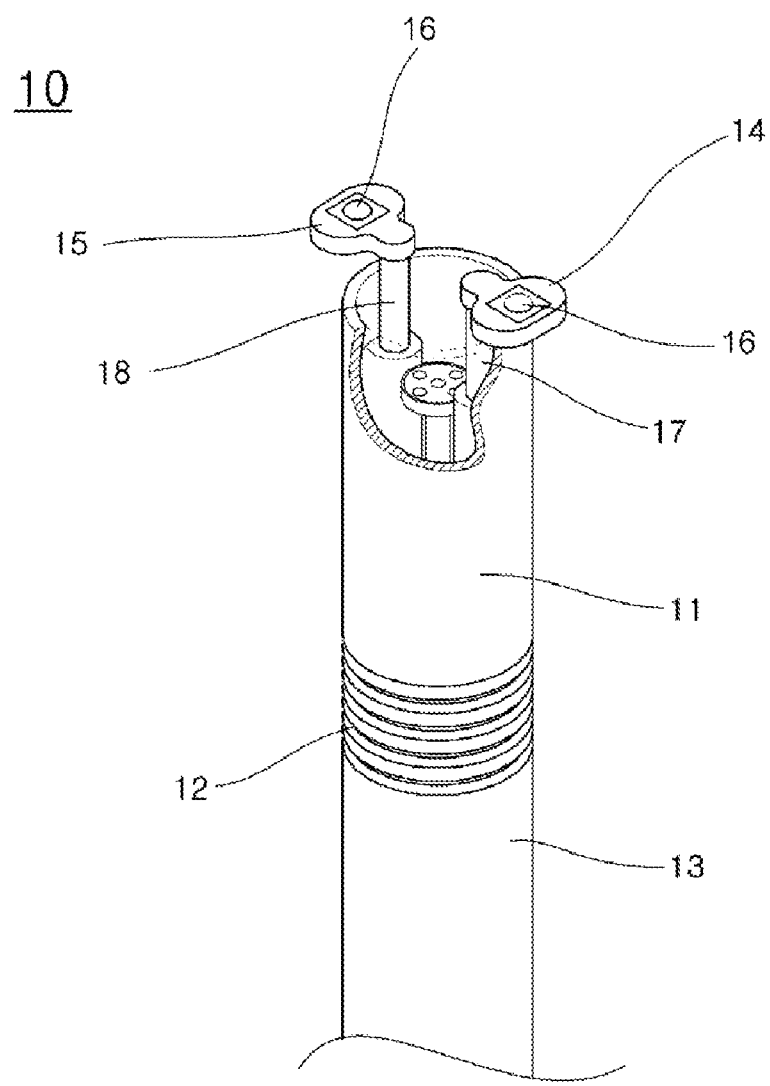
FIG. 2 is a diagram showing a conventional electronic endoscope providing three-dimensional image data.

That is, the conventional art has disadvantages in that, as shown in FIG. 1, the incision window for an endoscope and the incision window through which the therapeutic instrument is inserted need to be separately formed, or as shown in FIG. 2, the incision window needs to be largely formed in the patient's body since the endoscope device and the therapeutic instrument are horizontally formed on the same plane in one tube and thus the entire diameter of the tube is increased. However, the present invention has advantages in that the entire diameter of the main tube 100 can be formed to be small and the therapeutic instrument 600 having a larger diameter than the conventional art can be inserted inside the body, thereby performing various surgical operations, by installing the device for an endoscope and the therapeutic instrument in a line within one installation space.

Meanwhile, as shown in FIG. 4, as for a device for three-dimensional endoscopic surgery according to another embodiment of the present invention, first and second assisting devices 500a and 500b may be inserted between the second camera 300 and the therapeutic instrument 600, which are inserted inside the inner tube 110 of the main tube 100. When treatment such as surgery is performed using the therapeutic instrument 600, the first and second assisting devices 500a and 500b perform assistance while the main tube 100 is inserted into the body.

Here, robotic arms which are moved by electric power may be basically used for the first and second assisting devices 500a and 500b. In cases where these robotic arms need to be precisely driven during the surgery or treatment, the robotic arms may be configured to be driven by hydraulic or pneumatic pressure.

Therefore, the device for three-dimensional endoscopic surgery 1 according to the present invention as described above includes the first camera 200, the light source part 400, the second camera 300, the first assisting device 500a, the second assisting device 500b, and the therapeutic instrument 600, which are inserted in a line from the outside in the main tube 100. The first camera 200, the light source part 400, the second camera 300, and the first and second assisting devices 500a and 500b are respectively connected to first to fifth shafts 130a, 130b, 130c, 130d, and 130e. The first to fifth shafts 130a, 130b, 130c, 130d, and 130e serve to raise, lower, and rotate the elements respectively connected thereto.

That is, the first to fifth shafts 130a, 130b, 130c, 130d, and 130e are, respectively, connected to side portions of the first camera 200, the light source part 400, the second camera 300, and the first and second assisting devices 500a and 500b in order, and the elements respectively connected to the first to fifth shafts 130a, 130b, 130c, 130d, and 130e are raised, lowered, and rotated by driving of the first to fifth shafts 130a, 130b, 130c, 130d, and 130e.

Here, the therapeutic instrument 600 positioned at the innermost of the main tube 100 can be raised or lowered by a driving unit (not shown) such as a piston connected to a lower surface thereof, and thus a separate shaft is not needed.

More specifically, the first to fifth shafts 130a, 130b, 130c, 130d, and 130e are inserted into installation grooves 122 formed in the inner circumferential surface of the outer tube 120, and respectively connected to lateral surfaces of the first camera 200, the light source part 400, the second camera 300, and the first and second assisting devices 500a and 500b by connection members 140. The installation grooves 122 are formed in the outer circumferential surface of the outer tube 120 and spaced apart from each other at intervals of 72 degrees, so that the first to fifth shafts 130a, 130b, 130c, 130d, and 130e are inserted into the installation grooves 122 and spaced apart from each other at predetermined intervals.

In addition, guide slits 112 are formed in the inner tube 110 corresponding to the formation positions of the installation grooves 122 to allow the connection members 140 to move by the up-and-down driving of the first to fifth shafts 130a, 130b, 130c, 130d, and 130e.

Meanwhile, as shown in FIG. 11, the first to fifth shafts 130 a, 130 b, 130 c, 130 d, and 130 e each are formed in a double structure of a first tube 132 and a second tube 134. The first tube 132 are respectively connected to the first camera 200, the light source part 400, the second camera 300, and the first and second assisting devices 500 a and 500 b, and serve as supports for allowing the first camera 200, the light source part 400, the second camera 300, and the first and second assisting devices 500 a and 500 b to be driven. The second tube 134 is inserted inside the first tube 132, and serves to provide a fluid, which is to be used in the washing module 700, through an inner empty space.

In addition, the first tubes 132 and the second tubes 134 are formed of an insulation-coated titanium pipe, and serve as conductors for providing power used in the first camera 200, the light source part 400, the second camera 300, and the first and second assisting devices 500a and 500b.

In addition, signal transmission conductors 136 are inserted into space portions between the first tubes 132 and the second tubes 134 to transmit image signals photographed by the first and second cameras 200 and 300 and driving signals of the first and second assisting devices 500a and 500b.

Meanwhile, as shown in FIGS. 12a to 12e and 13, as for a device for three-dimensional endoscopic surgery 1 according to another embodiment of the present invention, the first to fifth shafts 130 a, 130 b, 130 c, 130 d, and 130 e may be coupled integrally with the first camera 200, the light source part 400, the second camera 300, and the first and second assisting devices 500 a and 500 b, respectively. This case has an advantage in that separate spaces for installing the first to fifth shafts 130 a, 130 b, 130 c, 130 d, and 130 e need not be formed in the inner tube 110 and the outer tube 120 constituting the main tube 100.

That is, as shown in FIG. 12(a) to (e), the first camera 200, the light source part 400, the second camera 300, and the first and second assisting devices 500a and 500b have one, two, three, four, or five coupling holes 150, with which the first to fifth shafts 130a, 130b, 130c, 130d, and 130e are coupled and which are formed from the outside thereof according to installation positions of the first to fifth shafts 130a, 130b, 130c, 130d, and 130e. The first camera 200 installed at the outermost position has one coupling hole 150 with which the first shaft 130a is coupled. The second assisting device 500b installed at the innermost position, except for the therapeutic instrument to which the shaft 130 is not connected, has four coupling holes 150' through which the first to fourth shafts 130a,130b,130c, and 130d pass and one coupling hole 150 with which the fifth shaft 130e is coupled.

Here, the second assisting device 500b is configured such that the four coupling holes 150' through which the first to fourth shafts 130a, 130b, 130c, and 130d pass are larger than the diameters of the first to fourth shafts 130a, 130b, 130c, and 130d, so that the second assisting device 500b is not movable even during the forward, backward, or rotational driving of the first to fourth shafts 130a, 130b, 130c, and 130d.

Rotation driving devices 800 for the rotational driving of the first camera 200, the light source part 400, the second camera 300, and the first and second assisting devices 500a and 500b are installed at the first to fifth shafts 130a, 130b, 130c, 130d, and 130e, respectively. The rotation driving device 800 includes a permanent magnet 810 and an electromagnet 820 on which a coil is wound.

That is, the first camera 200, the light source part 400, the second camera 300, and the first and second assisting devices 500a and 500b are sequentially forward driven to move outside the main tube 100 while being inserted into the patient's body. Here, in order to allow the instruments inserted in the back position to move outside the main tube 100, the instruments which first move outside the main tube 100 need to rotate in one direction to secure a space through which the instruments inserted into the back position can move outside the main tube 100, therefore, devices for the rotational driving of the first to fifth shafts 130a, 130b, 130c, 130d, and 130e are needed.

More specifically, the permanent magnet 810 is formed in a hollow cylindrical shape and fit-coupled with the outer circumferential surface of each of the first to fifth shafts 130a, 130b, 130c, 130d, and 130e, and the half of the permanent magnet 810, that is, a region corresponding to 0 to 180 degrees of the permanent magnet 810 has an N polarity and the other half of the permanent magnet 810 has an S polarity, so that the permanent magnet 810 is rotated by 180 degrees by magnetization of the electronic magnet 820, thereby rotating each of the first to fifth shafts 130a, 130b, 130c, 130d, and 130e. The electronic magnet 820 is spaced apart outwardly from the permanent magnet 810 at a predetermined interval. The electronic magnet 810 is magnetized into N or S polarity depending on the flowing direction of the current supplied through a coil wound on an outer circumferential surface thereof, thereby rotating the permanent magnet 810 fit-coupled with the outer circumferential surface of each of the first to fifth shafts 130a, 130b, 130c, 130d, and 130e and thus rotating each of the first to fifth shafts 130a, 130b, 130c, 130d, and 130e.

Here, the permanent magnets 810 are fit-coupled with the first to fifth shafts 130a, 130b, 130c, 130d, and 130e, and thus move forward and backward by the forward and backward driving of the first to fifth shafts 130a, 130b, 130c, 130d, and 130e, but the rotational driving of the first camera 200, the light source part 400, the second camera 300, and the first and second assisting devices 500a and 500b is conducted at predetermined positions, that is, as shown in FIG. 4, only positions at which the first camera 200, the light source part 400, the second camera 300, and the first and second assisting devices 500a and 500b protrude outwardly of the main tube 100, and thus the electronic magnets 820 are inserted into only the inside of the outer tube 120 at which the first to fifth shafts 130a, 130b, 130c, 130d, and 130e are rotated.

Meanwhile, locking devices 900 may be connected to the first to fifth shafts 130a, 130b, 130c, 130d, and 130e to prevent the rotation thereof. When the main tube 100 is inserted into the patient's body and performs surgery, the locking devices 900 serve to fix the first camera 200, the light source part 400, the second camera 300, and the first and second assisting devices 500a and 500b so that the first camera 200, the light source part 400, the second camera 300, and the first and second assisting devices 500a and 500b cannot be further rotated.

More specifically, each of the locking devices 900 includes a connector 910, a locking lever 920, and a locking tube 930, as shown in FIGS. 15(a) and (b). The connectors 910 are respectively inserted into the first to fifth shafts 130a, 130b, 130c, 130d, and 130e to serve to connect the locking levers 920 and the first to fifth shafts 130a, 130b, 130c, 130d, and 130e. The locking levers 920 are connected to the first to fifth shafts 130a, 130b, 130c, 130d, and 130e by the connectors 910 to restrict the rotation of the first to fifth shafts 130a, 130b, 130c, 130d, and 130e. The locking tube 930 is connected to the rear of the main tube 100 to fix the locking lever 920. A "¬"-shaped lever groove 932 in which the locking lever 920 moves is formed in the locking tube 930.

That is, for example, as for the first camera 200 connected to the first shaft 130a, when the main tube 100 is inserted into the patient's body, the first shaft 130a is forward driven by using a driving device (not shown), thereby allowing the first camera 200 to protrude outwardly of the main tube 100, and then the first shaft 130a is rotated by 180 degrees by using the rotation driving device 800.

After that, when the locking lever 920 positioned at the end of a horizontal part of the "¬"-shaped lever groove 932 formed in the locking tube 930 is rotated and then pulled backwardly to be positioned in a vertical part of the lever groove 932, the locking lever 920 cannot be further rotated, and the first shaft 130a and the first camera 200 connected to the first shaft 130a are not further rotated and maintained at a fixed state.

In contrast, in cases where the first camera 200 is to be again positioned inside the main tube 100 after surgery, the locking member 920 positioned in the vertical part of the lever groove 932 is moved forwardly and then rotated to be positioned at the horizontal part of the lever groove 932. Then, the first shaft 130*a* is again rotated by 180 degrees by using the rotation driving device 800 to allow the first camera 200 to be positioned on the main tube 100, and then the first shaft 130*a* is driven backwardly by using the driving device, so that the first camera 200 is again inserted inside the main tube 100 and thus the main tube 100 returns to a state in which the main tube 100 is withdrawable from the patient's body.

Meanwhile, in cases where the main tube 100 consists of the inner tube 110 and the outer tube 120, as described above, and the first camera 200, the light source part 400, the second camera 300, and the first and second assisting devices 500*a* and 500*b* are respectively connected to the first to fifth shafts 130*a*, 130*b*, 130*c*, 130*d*, and 130*e* by the connection members 140, surgical instruments can be fixed during the surgery by forming fixing grooves 124, into which the connection members 140 are inserted, in the outer circumferential surface of the upper end of the outer tube 120.

That is, as shown in FIGS. 6(*a*) and (*b*) and FIG. 8, for example, as for the first camera 200 connected to the first shaft 130*a*, in cases where the main tube 100 is inserted into the patient's body, the first shaft 130*a* is driven forwardly by using the driving device (not shown) to allow the first camera 200 to protrude outwardly of the main tube 100, and the first shaft 130*a* is rotated by about 180 degrees by using the rotation driving device 800 and then pulled backwardly, the connection member 140 provided between the first shaft 130*a* and the first camera 200 is fit-coupled with the fixing groove 124 formed in the outer circumferential surface of the upper end of the outer tube 120 and thus cannot be rotated, so that the first camera 200 can be fixed so as not to rotate or move during the surgery.

Meanwhile, the foregoing embodiments have been described based on the main tube 100 formed in a double structure of the inner tube 110 and the outer tube 120, but the main tube 100 may be formed as a single tube and the shafts 130 may be inserted inside the main tube 100.

Also in this case, guide slits for allowing the connection members 140 to move may be formed in the inner circumferential surface of the main tube 100, and fixing grooves with which the connection members 140 are insert-coupled may be formed in the outer circumferential surface of the upper end of the main tube 100.

In addition, even in cases where the first to fifth shafts 130*a*, 130*b*, 130*c*, 130*d*, and 130*e* are integrally coupled with the first camera 200, the light source part 400, the second camera 300, and the first and second assisting devices 500*a* and 500*b*, respectively, the main tube 100 may be formed in a single-tube shape rather than a double-pipe shape.

Therefore, according to the device for three-dimensional endoscopic surgery 1 of the present invention as described above, the therapeutic instruments including the endoscope can be inserted into the human body through one main tube 100 and can be spread outward to be utilized in the human body, thereby minimizing an incision site at the time of surgery, utilizing natural openings without separate incision windows, and performing various medical works using one main tube 100. Further, the endoscope consisting of the cameras 200 and 300 and the light source part 400 and the therapeutic instrument 600 for performing medical works are sequentially inserted inside the main tube 100, thereby installing the larger therapeutic instrument 600 inside the main tube 100 and thus performing various medical works. Further, the washing modules 700 for washing the cameras 200 and 300 and the light source part 400 are provided inside the main tube 100, thereby providing clearer three-dimensional images during performing of medical works.

Although the preferable embodiments of the present invention have been described, the present invention is not limited to the above embodiments, and it is obvious to those skilled in the art that various changes and modifications can be made within the technical scope of the present invention.

The present invention is directed to a device for three-dimensional endoscopic surgery, and more specifically, to a device for three-dimensional endoscopic surgery in which therapeutic instruments including an endoscope can be inserted into the human body through one main tube and can be spread outward to be utilized in the human body, thereby minimizing an incision site at the time of surgery and performing various medical works using one main tube.

The invention claimed is:

1. A device for three-dimensional endoscopic surgery comprising:
  a main tube configured to be inserted into a patient's body; and
  first and second cameras, a light source part, and a therapeutic instrument inserted in a line inside the main tube;
  wherein the main tube consists of an inner tube and an outer tube,
  wherein shafts are between the inner tube and the outer tube
  wherein the shafts are respectively connected to the first and second cameras, and the light source part by connection members, wherein the shafts are slidably disposed within installation holes formed in an inner circumferential surface of the outer tube, and wherein the connection members are configured to slidably engage slits formed in the inner tube,
  wherein connection members are configured to matingly engage fixing grooves formed in an outer circumferential surface of a distal end of the outer tube.

2. The device of claim 1, wherein the light source part is inserted between the first and second cameras.

3. The device of claim 1, wherein the therapeutic instrument is positioned proximal to the second camera and inserted inside the main tube.

4. The device of claim 3, wherein first and second assisting devices are inserted between the second camera and the therapeutic instrument.

5. The device of claim 4, wherein first to fifth shafts respectively coupled with the first and second cameras, the light source part, and the first and second assisting devices are inserted between the inner tube and the outer tube.

6. The device of claim 5, wherein the first to fifth shafts are respectively connected to the first and second cameras, the light source part, and the first and second assisting devices by connection members wherein installation holes with which the first to fifth shafts are insert-coupled are formed in an inner circumferential surface of the outer tube, and wherein the connection members are configured to slidably engage guide slits formed in the inner tube.

7. The device of claim 5, wherein coupling holes with which the shafts are insert-coupled are formed in the first and second cameras, the light source part, and the first and second assisting devices.

8. The device of claim 5, wherein each of the first to fifth shafts includes a first tube connected to each of the first and second cameras, the light source part, and the first and second assisting devices and a second tube inserted inside the first tube.

9. The device of claim 8, wherein a signal transmission conductor for transmitting image signals and driving signals is inserted between the first tube and the second tube.

10. The device of claim 8, wherein the first and second tubes are formed of an insulation-coated titanium pipe.

11. The device of claim 5, wherein permanent magnets are configured to slidably engage with outer circumferential surfaces of the first to fifth shafts and electronic magnets having coils wound thereon are provided inside the outer tube spaced apart from the permanent magnets at predetermined intervals.

12. The device of claim 5, wherein locking devices are connected to the first to fifth shafts for preventing rotation of the first to fifth shafts.

13. The device of claim 12, wherein each of the locking devices includes a connector inserted into each of the first to fifth shafts, a locking lever connected to the connector, and a locking tube having a ¬'-shaped lever groove in which the locking lever is moved.

14. The device of claim 4, wherein the first and second assisting devices are formed of robotic arms.

15. The device of claim 1, wherein the first and second cameras include lens mounts on which lenses are fixed, image sensors installed at the rear of the lenses, and lens driving devices positioned at the rear of the image sensors and connected to the lens mounts.

16. The device of claim 15, wherein the image sensors consist of photosensors at the center thereof and signal connectors provided outside the photosensors, the signal connectors being bent in opposite directions of the lenses.

17. The device of claim 1, wherein washing modules for washing lenses are provided in the first and second cameras and the light source part.

\* \* \* \* \*